US010004650B2

(12) United States Patent
Guertin et al.

(10) Patent No.: US 10,004,650 B2
(45) Date of Patent: Jun. 26, 2018

(54) DYNAMIC PATIENT POSITIONING SYSTEM

(75) Inventors: Timothy E. Guertin, Saratoga, CA (US); Marcel R. Marc, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1912 days.

(21) Appl. No.: 11/985,814

(22) Filed: Nov. 16, 2007

(65) Prior Publication Data

US 2008/0071420 A1    Mar. 20, 2008

Related U.S. Application Data

(63) Continuation-in-part of application No. 11/415,974, filed on May 1, 2006, now Pat. No. 7,640,607, and a (Continued)

(51) Int. Cl.
| | |
|---|---|
| *A61G 1/017* | (2006.01) |
| *A61G 1/02* | (2006.01) |
| *A61G 5/04* | (2013.01) |
| *A61N 5/10* | (2006.01) |
| *G06F 19/00* | (2018.01) |

(Continued)

(52) U.S. Cl.
CPC .......... *A61G 1/017* (2013.01); *A61G 1/0212* (2013.01); *A61G 1/0231* (2013.01); *A61G 1/0275* (2013.01); *A61G 1/0293* (2013.01); *A61G 5/046* (2013.01); *A61N 5/1049* (2013.01); *A61N 5/1079* (2013.01); *G06F 19/3481* (2013.01); *G06Q 50/22* (2013.01); *A61G 5/006* (2013.01); *A61G 2200/325* (2013.01); *A61G 2210/50* (2013.01); *A61N 2005/1063* (2013.01); *G06F 19/327* (2013.01); *G16H 40/20* (2018.01)

(58) Field of Classification Search
CPC ........ G06Q 50/22; G06Q 50/24; G06Q 40/08; G06Q 10/10; G06F 19/322
USPC .............................................. 705/2; 250/250
See application file for complete search history.

(56) References Cited

U.S. PATENT DOCUMENTS

| | | |
|---|---|---|
| 3,133,227 A | 5/1964 | Brown et al. |
| 3,144,552 A | 8/1964 | Schonberg et al. |

(Continued)

FOREIGN PATENT DOCUMENTS

| | | |
|---|---|---|
| AU | 746987 B2 | 2/2000 |
| AU | 2002215340 B2 | 4/2005 |

(Continued)

OTHER PUBLICATIONS

EPO, European Search Report in European Application No. 07 86 2095, Dec. 2, 2013, 11 pages.

(Continued)

*Primary Examiner* — Tran N Nguyen
(74) *Attorney, Agent, or Firm* — Houst Consulting

(57) ABSTRACT

A patient treatment system includes one or more automated patient transporters configured to move a patient from a preparation area to one of a plurality of alternative treatment areas, and to position the patient relative to a therapeutic radiation beam. Both transportation of the patient and positioning of the patient are optionally performed while the patient is secured to one of the patient transporters. A control system may be used to both position and transport the patient responsive to a patient treatment plan.

29 Claims, 5 Drawing Sheets

Related U.S. Application Data continuation-in-part of application No. 11/447,532, filed on Jun. 5, 2006, now Pat. No. 7,547,901.

(60) Provisional application No. 60/859,675, filed on Nov. 17, 2006, provisional application No. 60/676,138, filed on Apr. 29, 2005.

(51) Int. Cl.
| | |
|---|---|
| *G06Q 50/22* | (2018.01) |
| *A61G 5/00* | (2006.01) |
| *G16H 40/20* | (2018.01) |

(56) References Cited

U.S. PATENT DOCUMENTS

| | | | |
|---|---|---|---|
| 3,193,717 | A | 7/1965 | Nunan |
| 3,987,281 | A | 10/1976 | Hodes |
| 4,149,247 | A | 4/1979 | Pavkovich et al. |
| 4,149,248 | A | 4/1979 | Pavkovich |
| 4,208,675 | A | 6/1980 | Bajon et al. |
| 4,209,706 | A | 6/1980 | Nunan |
| 4,521,808 | A | 6/1985 | Ong et al. |
| 4,547,892 | A | 10/1985 | Richey et al. |
| 4,593,967 | A | 6/1986 | Haugen |
| 4,628,523 | A | 12/1986 | Heflin |
| 4,675,731 | A | 6/1987 | Takasu et al. |
| 4,679,076 | A | 7/1987 | Vikterlof et al. |
| 4,726,046 | A | 2/1988 | Nunan |
| 4,741,621 | A | 5/1988 | Taft et al. |
| 4,825,393 | A | 4/1989 | Nishiya |
| 4,853,777 | A | 8/1989 | Hupp |
| 4,868,843 | A | 9/1989 | Nunan |
| 4,868,844 | A | 9/1989 | Nunan |
| 4,949,408 | A * | 8/1990 | Trkla ............... 5/86.1 |
| 5,001,344 | A | 3/1991 | Kato et al. |
| 5,014,292 | A | 5/1991 | Siczek et al. |
| 5,027,818 | A | 7/1991 | Bova et al. |
| 5,039,867 | A | 8/1991 | Nishihara et al. |
| 5,080,100 | A | 1/1992 | Trotel |
| 5,099,505 | A | 3/1992 | Seppi et al. |
| 5,117,445 | A | 5/1992 | Seppi et al. |
| 5,117,829 | A * | 6/1992 | Miller et al. ............ 600/427 |
| 5,157,707 | A | 10/1992 | Ohlson |
| 5,161,546 | A * | 11/1992 | Bronn ............... A61N 5/10 128/897 |
| 5,168,532 | A | 12/1992 | Seppi et al. |
| 5,247,555 | A | 9/1993 | Moore et al. |
| 5,262,649 | A | 11/1993 | Antonuk et al. |
| 5,332,908 | A | 7/1994 | Weidlich |
| 5,335,255 | A | 8/1994 | Seppi et al. |
| 5,379,468 | A | 1/1995 | Cassidy et al. |
| 5,394,452 | A | 2/1995 | Swerdloff et al. |
| 5,400,255 | A | 3/1995 | Hu |
| 5,411,026 | A | 5/1995 | Carol |
| 5,438,991 | A | 8/1995 | Yu et al. |
| 5,471,516 | A | 11/1995 | Nunan |
| 5,471,546 | A | 11/1995 | Meier |
| 5,509,042 | A | 4/1996 | Mazess |
| 5,521,957 | A | 5/1996 | Hansen |
| 5,537,452 | A | 7/1996 | Shepherd et al. |
| 5,591,983 | A | 1/1997 | Yao |
| 5,622,187 | A * | 4/1997 | Carol ............... A61N 5/1049 128/897 |
| 5,647,663 | A | 7/1997 | Holmes |
| 5,661,773 | A | 8/1997 | Swerdloff et al. |
| 5,663,995 | A | 9/1997 | Hu |
| 5,663,999 | A | 9/1997 | Siochi |
| 5,673,300 | A | 9/1997 | Reckwerdt et al. |
| 5,675,625 | A | 10/1997 | Rockseisen |
| 5,692,507 | A | 12/1997 | Seppi et al. |
| 5,719,914 | A | 2/1998 | Rand et al. |
| 5,724,400 | A | 3/1998 | Swerdloff et al. |
| 5,748,700 | A | 5/1998 | Shepherd et al. |
| 5,748,703 | A | 5/1998 | Cosman |
| 5,748,907 | A * | 5/1998 | Crane ............... 705/2 |
| 5,751,781 | A | 5/1998 | Brown et al. |
| 5,757,881 | A | 5/1998 | Hughes |
| 5,802,136 | A | 9/1998 | Carol |
| 5,818,902 | A | 10/1998 | Yu |
| 5,835,558 | A | 11/1998 | Maschke |
| 5,842,987 | A | 12/1998 | Sahadevan |
| 5,848,126 | A | 12/1998 | Fujita et al. |
| 5,851,182 | A | 12/1998 | Sahadevan |
| 5,877,501 | A | 3/1999 | Ivan et al. |
| 5,858,891 | A | 6/1999 | Hibbard |
| 5,912,943 | A | 6/1999 | Deucher et al. |
| 5,926,521 | A | 7/1999 | Tam |
| 5,929,449 | A | 7/1999 | Huang |
| 5,949,811 | A | 9/1999 | Baba et al. |
| 5,956,382 | A | 9/1999 | Wiener-Avnear et al. |
| 5,960,055 | A | 9/1999 | Samarasekera et al. |
| 5,999,587 | A | 12/1999 | Ning et al. |
| 6,031,888 | A | 2/2000 | Ivan et al. |
| 6,038,283 | A | 3/2000 | Carol et al. |
| 6,041,097 | A | 3/2000 | Roos et al. |
| 6,075,836 | A | 6/2000 | Ning |
| 6,078,638 | A | 6/2000 | Sauer et al. |
| 6,104,778 | A | 8/2000 | Murad |
| 6,104,780 | A | 8/2000 | Hanover et al. |
| 6,108,400 | A | 8/2000 | Siochi |
| 6,113,264 | A | 9/2000 | Watanabe |
| 6,134,296 | A | 10/2000 | Siochi |
| 6,142,925 | A | 11/2000 | Siochi et al. |
| 6,144,875 | A | 11/2000 | Schweikard et al. |
| 6,148,058 | A | 11/2000 | Dobbs |
| 6,152,598 | A | 11/2000 | Tomisaki et al. |
| 6,200,024 | B1 | 3/2001 | Negrelli |
| 6,219,403 | B1 | 4/2001 | Nishihara |
| 6,219,441 | B1 | 4/2001 | Hu |
| 6,222,901 | B1 | 4/2001 | Meulenbrugge et al. |
| 6,240,161 | B1 | 5/2001 | Siochi |
| 6,260,005 | B1 | 7/2001 | Yang et al. |
| 6,269,141 | B1 | 7/2001 | Proksa et al. |
| 6,269,143 | B1 | 7/2001 | Tachibana |
| 6,278,766 | B1 | 8/2001 | Kooy et al. |
| 6,285,739 | B1 | 9/2001 | Rudin et al. |
| 6,292,526 | B1 | 9/2001 | Patch |
| 6,307,914 | B1 | 10/2001 | Kunieda et al. |
| 6,314,159 | B1 | 11/2001 | Siochi |
| 6,318,892 | B1 | 11/2001 | Suzuki et al. |
| 6,325,537 | B1 | 12/2001 | Watanabe |
| 6,325,758 | B1 | 12/2001 | Carol et al. |
| 6,330,300 | B1 | 12/2001 | Siochi |
| 6,335,961 | B1 | 1/2002 | Wofford et al. |
| 6,345,114 | B1 | 2/2002 | Mackie et al. |
| 6,349,129 | B1 | 2/2002 | Siochi |
| 6,353,222 | B1 | 3/2002 | Dotan |
| 6,370,421 | B1 | 4/2002 | Williams et al. |
| 6,381,302 | B1 | 4/2002 | Berestov |
| 6,385,286 | B1 | 5/2002 | Fitchard et al. |
| 6,385,288 | B1 | 5/2002 | Kanematsu |
| 6,385,477 | B1 | 5/2002 | Werner et al. |
| 6,393,096 | B1 | 5/2002 | Carol et al. |
| 6,405,072 | B1 | 6/2002 | Cosman |
| 6,411,675 | B1 | 6/2002 | Llacer |
| 6,429,578 | B1 | 8/2002 | Danielsson et al. |
| 6,435,715 | B1 | 8/2002 | Betz et al. |
| 6,438,202 | B1 | 8/2002 | Olivera et al. |
| 6,445,766 | B1 | 9/2002 | Whitham |
| 6,463,122 | B1 | 10/2002 | Moore |
| 6,473,490 | B1 | 10/2002 | Siochi |
| 6,480,565 | B1 | 11/2002 | Ning |
| 6,490,476 | B1 | 12/2002 | Townsend et al. |
| 6,502,261 | B1 | 1/2003 | Harwood |
| 6,504,892 | B1 | 1/2003 | Ning |
| 6,508,586 | B2 | 1/2003 | Oota |
| 6,560,311 | B1 | 5/2003 | Shepard et al. |
| 6,590,953 | B2 | 7/2003 | Suzuki et al. |
| 6,611,700 | B1 * | 8/2003 | Vilsmeier et al. ............ 600/407 |
| 6,618,467 | B1 | 9/2003 | Ruchala et al. |
| 6,621,889 | B1 | 9/2003 | Mostafavi |
| 6,640,364 | B1 * | 11/2003 | Josephson et al. ............ 5/601 |
| 6,661,870 | B2 | 12/2003 | Kapatoes et al. |

(56) References Cited

U.S. PATENT DOCUMENTS

| | | | |
|---|---|---|---|
| 6,744,848 B2 | 6/2004 | Stanton et al. | |
| 6,842,502 B2 | 1/2005 | Jaffray et al. | |
| 6,865,254 B2 | 3/2005 | Nafstadius | |
| 6,888,919 B2 | 5/2005 | Graf | |
| 6,914,959 B2 | 7/2005 | Bailey et al. | |
| 7,397,044 B2* | 7/2008 | Calderon | A61N 5/1048 250/370.08 |
| 7,640,607 B2* | 1/2010 | Guertin et al. | 5/601 |
| 7,945,021 B2 | 5/2011 | Shapiro et al. | |
| 8,116,430 B1 | 2/2012 | Shapiro et al. | |
| 2001/0001807 A1 | 5/2001 | Green | |
| 2001/0008271 A1 | 7/2001 | Ikeda et al. | |
| 2002/0006182 A1 | 1/2002 | Kim et al. | |
| 2002/0066860 A1 | 6/2002 | Possin | |
| 2002/0077749 A1* | 6/2002 | Doi | 701/209 |
| 2002/0120986 A1* | 9/2002 | Erbel | A61B 6/0421 5/601 |
| 2002/0179812 A1 | 12/2002 | Kochi et al. | |
| 2003/0007601 A1 | 1/2003 | Jaffray et al. | |
| 2004/0220467 A1* | 11/2004 | Bonutti | A61B 5/0555 600/407 |
| 2005/0138732 A1 | 6/2005 | Erbel et al. | |
| 2006/0118736 A1 | 6/2006 | Moriyama et al. | |

FOREIGN PATENT DOCUMENTS

| | | |
|---|---|---|
| DE | 3828639 A1 | 3/1989 |
| DE | 4223488 A1 | 1/1994 |
| DE | 19614643 | 10/1997 |
| EP | 0062941 A1 | 10/1982 |
| EP | 0062941 B1 | 9/1984 |
| EP | 0205720 A1 | 12/1986 |
| EP | 0480035 A1 | 4/1992 |
| EP | 0480035 B1 | 11/1994 |
| EP | 713677 A1 | 5/1996 |
| EP | 656797 B1 | 9/1998 |
| EP | 0922943 A2 | 6/1999 |
| EP | 0948930 A1 | 10/1999 |
| EP | 810006 B1 | 8/2000 |
| EP | 1095628 | 5/2001 |
| EP | 965104 B1 | 9/2001 |
| EP | 471455 B2 | 4/2002 |
| FR | 2269745 A1 | 11/1975 |
| FR | 2551664 A1 | 3/1985 |
| GB | 1328033 A | 8/1973 |
| JP | 58-94835 | 6/1983 |
| JP | 63-294839 A | 12/1988 |
| JP | 1040069 A | 2/1989 |
| JP | 11-62682 A | 6/1989 |
| JP | 50-57028 | 3/1993 |
| JP | 59000076 A | 1/1994 |
| JP | 06-79006 A | 3/1994 |
| JP | 06-339541 A | 12/1994 |
| JP | 07-255717 A | 10/1995 |
| JP | 9239044 A | 9/1997 |
| JP | 9327453 A | 12/1997 |
| JP | 10-113400 A | 5/1998 |
| JP | 10-511595 A | 11/1998 |
| JP | 10-328318 A | 12/1998 |
| JP | 11-99148 | 4/1999 |
| JP | 11-160440 A | 6/1999 |
| JP | 2000116638 A | 4/2000 |
| JP | 2000140137 A | 5/2000 |
| JP | 2000152927 | 6/2000 |
| JP | 2000317000 A | 11/2000 |
| JP | 2001029489 A | 2/2001 |
| JP | 2001029491 A | 2/2001 |
| JP | 2001095793 A | 4/2001 |
| JP | 2001120528 A | 5/2001 |
| WO | 1985/003212 A1 | 8/1985 |
| WO | 1990/014129 A1 | 11/1990 |
| WO | 1992/000567 A1 | 1/1992 |
| WO | 1992/002277 A1 | 2/1992 |
| WO | 1992/020202 A1 | 11/1992 |
| WO | 1995/000204 A1 | 1/1995 |
| WO | 1997/013552 | 4/1997 |
| WO | 1997/042522 | 11/1997 |
| WO | 1998/052635 | 11/1998 |
| WO | 1999/003397 A1 | 1/1999 |
| WO | 1999/048558 A1 | 9/1999 |
| WO | 2000/015299 A1 | 3/2000 |
| WO | 2001/060236 A2 | 8/2001 |
| WO | 2002/013907 A1 | 2/2002 |
| WO | 2002/024277 A1 | 3/2002 |
| WO | 2002/061680 A2 | 8/2002 |

OTHER PUBLICATIONS

PCT. International Search Report and Written Opinion in PCT Application PCT/US07/24103, May 5, 2008, 8 pages.

Simo Muinonen, Säadehoiden valmistelun optimointi fysiikan keinoin, 1995, pp. 1-166.

Jyrki Alakuijala, Algorithms for modeling anatomic and target volumes in image-guided neurosurgery and radiotherapy, 2001, pp. 1-121.

Intensiteettimuokattu sädehoito—uusi tekniikka parantanee hoitotuloksia, 2001, Heikki Joensuu, Mauri Kouri, Mikko Tenhunen, pp. 389-394.

Tiina Seppälä, FiR 1 epithermal neutron beam model and dose calculation for treatment planning in neutron capture therapy, 2002, pp. 1-46.

Maria Korteila, Varianin avulla säde tappaa kasvaimen tarkasti, 2000, pp. 1-8.

Budgell, Temporal resolution requirements for intensity modulated radiation therapy delivered by multileaf collimators, 1999, pp. 1581-1596.

Xing et al, Dosimetric verification of a commercial inverse treatment planning system, 1999, pp. 463-478.

Johan Löt Development of a general framework for optimization of radiation therapy, 2000, pp. 1-140.

Xing et al, Iterative methods for inverse treatment planning, 1996, pp. 2107-2123.

Jinho LimOptimization in radiation treatment planning, 2002.

Podgorsak et al, Dynamic Stereotactic Radiosurgery, 1988, pp. 115-126.

Webb et al, Inverse planning with constraints to generate smoothed intensity-modulated beams, 1998, pp. 2785-2794.

Crooks et al, Linear algebraic methods applied to intensity modulated radiation therapy, 2001, pp. 2587-2606.

Digital Imaging and Communications in Medicine (DICOM) Supplement 11 Radiotherapy Objects, 1997, pp. 1-103.

Anderson, R., Software system for automatic parameter logging on Philips SL20 linear accelerator, 1995, pp. 220-222.

Berkeshev, O.S. et. al., Practical realization of a method of digital x-ray diagnostics in a scanning-type device[3], 2001, pp. 36-37.

Jaffray, et al., Cone-beam computed tomography on a medical linear accelerator using a flat-panel imager, 2000, pp. 558-560.

Karzmark, C.J., A Primer on Theory and Operation of Linear Accelerators in Radiation Therapy, Dec. 1981, pp. 1-61.

Wong, J. et al., Behandlung des Lungenkarzinoms mittels stereotaktischer Strahlentherapie unter Verwednung des weltweit ersten PRIMATOM Systems—eine Fallstudie[4], 2001, pp. 133-136.

Studholme et al., Automated three-dimensional registration of magnetic resonance and positron emission tomography brain images by multiresolution optimization of voxel similarity measures, 1997, pp. 25-35.

"Advanced Workstation for Irregular Field Simulation and Image Matching," Copyright 1999, MDS Nordion, 7 pages.

Andrew, J. W. et al., "A video-based patient contou acquisition system for the design radiotherapy compensators," Abstract, Med Phys, May-Jun. 1989, vol. 16 (3), pp. 425-430.

Balter, J M., et al., "Daily Targeting of intrahepatic tumors for Radiotherapy", Int. J. Radiation Oncology Biol. Phys., vol. 52, No. 1, (2002), 266-271.

(56) References Cited

OTHER PUBLICATIONS

Elliot, et al., "Interactive Imagine Segmentation for Radiation Treatment Planning", Abstract, IBM Systems Journal, vol. 31, No. 4, (1992), 620-634.

Fahrig, R., et al., "Three-Dimensional Computed Tomographic Reconstruction Using a C-Arm Mounted XRII: Image Based Correction of Gantry Motion Nonidealities", Med. Phys., vol. 27, No. 1, (Jan. 2000), 30-38.

Feldkamp, L A., et al., "Practical Cone-Beam Algorithm", J. Opt. Soc. Am. A, vol. 1, No. 6, (Jun. 1984), 612-619.

Gadermann, et al., "Three-dimensional radiation planning. Studies on clinical integration," Abstract, Strahlenther Onkol, 1993, vol. 169 (3), pp. 159-167.

Groh, B A., et al., "A Performance Comparison of Flat-Panel Imager-Based MV and kV Conebeam CT", Med. Phys., vol. 29, No. 6, (Jun. 2002), 967-975.

Hara et al., "Radiotherapeutic System," 00480035/EP-B1, Citation from World Patent, 1994, 1 page.

Kushima, GJ, et al., "New Development of Integrated CT Simulation System for Radiation Therapy Planning", Abstract. Kobe J. Med. Sci., vol. 9, No. 5-6, (Dec. 1993), 17-213.

Kutcher, et al., "Three dimensional radiation treatment planning," Abstract (1998), Dosimetry in radiotherapy, vol. 2, Proceedings of an international symposium held in Vienna, Austria, Aug.-Sep. 1987.

Masahiro et al., "Patient Beam Positioning System Using CT Images", Phys. Med. Biol., 1982, vol. 27, No. 2, pp. 301-305, printed in Great Britain.

Ragan, "Correction for Distortion in a Beam Outline Transfer Device in Radiotherapy CT-Based Simulation," Med. Phys. 20 (1), Jan./Feb. 1993, pp. 179-185.

Redpath, et al., "Use of a simulator and treatment planning computer as a CT scanner for radiotherapy planning," Abstract, Proceedings—Eighth International Conference on the Use of Computers in Radiation Therapy held in Toronto, Canada, 1984, pp. 281-287. IEEE, New York, NY.

Reynolds, et al., "An algorithm for three-dimensional visualization of radiation therapy beams," Abstract, Jan.-Feb. 1988, vol. 15 (1), pp. 24-28.

Rizo et al., "Comparison of two three-dimensional x-ray cone-beam-reconstruction algorithms with circular source trajectories," J. Opt. Soc. Am. A, 10, 1639 (1991).

Ruchala, K J., et al., "Megavoltage CT Tomography System", Phy. Med. Biol., vol. 44, (1999), 2597-2621.

Swindell, W, et al., "Computed Tomography with a Linear Accelerator with Radiotherapy Applications", Med. Phys., vol. 10, No. 4, (Jul./Aug. 1983), 416-420.

Uematsu, M, et al., "A Dual Computed Tomography Linear Accelerator Unit for Stereotactic Radiation Therapy: A New Approach Without Cranially Fixated Stereotactic Frames", Int. J. Radiation Oncology Biol. Phys., vol. 35, No. 3, (1996), pp. 587-592.

Uematsu, M, et al., "Infractional Tumor Position Stability During Computed Tomography (CT)—Guided Frameless Seterotactic Radiation Therapy for Lung or Liver cancers with a Fusion of CT and Linear Accelerator (FOCAL) Unit", Int. J. Radiation Oncology Biol. Phys, vol. 48, No. 2, (2000), 443-448.

Yan et al., "Derivation and analysis of a filtered backprojection algorithm for cone beam projection," IEEE Trans. Medical Imaging, 10, pp. 462-472 (1991).

Kuhn, M.H., AIM Project A2003: Computer Vision in RAdiology (COVIRA), Oct. 1994, pp. 17-31.

Kushima T. et al., New development of integrated CT simulation system for radiation therapy planning, 1993, pp. 197-213.

Kutcher, G. J. et al., Three dimensional radiation treatment planning, 1987.

Masahiro, et al., Patient Beam Positioning System Using CT Images, 1982, pp. 301-305.

Midgley, S. et al., A Feasibility Study for Megavoltage Cone Beam CT Using a Commercial EPID, 1998, pp. 155-169.

Mohan, R, et al., Intersection of shaped radiation beams with arbitrary image sections, Jun. 1987, pp. 161-168.

Nakagawa, Keiichi, M.D. et al., Megavoltage CT-Assisted Stereotactic Radiosurgery for Thoracic Tumors: Original Research in the Treatment of Thoracic Neoplasms, 2000, pp. 449-457.

Niemierko, A. et al., Random sampling for evaluation treatment plans, 1990, pp. 753-762.

Ning et al., Flat Panel Detector-Based Cone-Beam Volume CT Angiography Imaging: System Evaluation, Sep. 2000, pp. 949-963.

Ning et al., Image Intensifier-Based Volume Tomographic Angiography Imaging System: System Evaluation, 1995, pp. 280-290.

Spirou et al., A Gradient Inverse Planning Algorithm with Dose-Volume Contraints, 1998, pp. 321-333.

Spirou et al., Generation of Arbitrary Intensity Profiles by Dynamic Jaws or Multileaf Collimators, 1994, pp. 1031-1041.

Tervo et al., A Model for the Control of a Multileaf Collimator in Radiation Therapy Treatment Planning, 2000, pp. 1875-1895.

Uematsu, M. et al., A Dual Computed Tomography Linear Accelerator Unit for Stereotactic RadiationTherapy: A New Approach WithoutCranially Fixated Stereotactic Frames, 1996, pp. 587-592.

Uematsu, M. et al., Daily Positioning Accuracy of Frameless Stereotactic Radiation Therapy with a Fusion of Computed Tomography and Linear Accelerator (FOCAL) Unit: Evaluation of Z-axis with a Z-marker, Mar. 1999, pp. 337-339.

W. De Gersem et al., Leaf position optimization for step-and-shoot IMRT, 2001, pp. 1371-1388.

Wu et al., Algorithm and Functionality of an Intensity Modulated Radiotherapy Optimization System, 2000, pp. 701-711.

Xia et al., Multileaf Collimator Leaf Sequencing Algorithm for Intensity Modulated Beams with Multiple Static Segments, 1998, pp. 1424-1434.

Zellars, R.C. et al., Prostate position late in the course of external beam therapy: Patterns and predictors, 2000, pp. 655-660.

Rostkowska, J. et al., Physical and Dosimetric Aspects of QualityAssurance in Sterotactic Radiotherapy, 2001, pp. 53-54.

Sidhu, K. et al., Optimization of Conformal Thoracic Radiotherapy Plance While Using Cone—Beam CT Imaging for Treatment Verification, 2001, pp. 175-176.

Smith, R. et al., Development of cone beam CT for radiotherapy treatment planning, 2001, pp. S115.

Nag, S. et al., Intraoperative Planning and Evaluation of Permanent Prostate Brachytherapy: Report of the American Brachytherapy Society, 2001, pp. 1422-1430.

MacKenzie, M. and, Robinson, D., Intensity modulated arc deliveries approximated by a large number of fixed gantry position sliding window dynamic multileaf collimator fields, 2002, pp. 2359-2365.

Bissonnette, J-P, et, al., An Alternative X-Ray Detector for Portal Imaging: High Density Glass Scintillator, 1993, pp. 36-37.

Bissonnette, J-P, et. al., Physical characterization and optimal magnification of a portal imaging system, 1992, pp. 182-188.

Colbeth, R. et al., 40 x 30 cm Flat Panel Imager for Angiography, R&F, and Cone-Beam CT Applications, Feb. pp. 94-102.

Colbeth, R. et al., Characterization of an Amorphous Silicon Fluoroscopic Imager, 1997, pp. 42-51.

Colbeth, R. et al., Characterization of a third generation, multi-mode sensor panel, Feb. 1999, pp. 491-500.

Colbeth, R. et al., A Multi-mode X-ray Imager for Medical and Industrial Applications, 1998, pp. VI-629-VI-632.

Colbeth, R. et al., Flat panel imaging system for fluoroscopy applications, Feb. 1998, pp. 376-387.

Gilblom, D. et al., Real-time x-ray imaging with flat panels, 1998, pp. 213-223.

Gilblom, D. et al., A real-time, high-resolution camera with an amorphous silicon large-area sensor, 1998, pp. 29-38.

Jaffray, D. et al., Medical linear accelerator x-ray sources: Variation with make, model, and time, 1992, pp. 174-181.

Johnsen, S. et al., Improved Clinac Electron Beam Quality, 1983, pp. 737.

Klausmeier-Brown, M.E. et al., Real-Time Image Processing in a Flat-Panel, Solid-State, Medical Fluoroscopic Imaging System, Jan. 1998, pp. 2-7.

(56) References Cited

OTHER PUBLICATIONS

Kubo, H., Potential and role of a prototype amorphous silicon array electronic portal imaging device in breathing synchronized radiotherapy, Nov. 1999, pp. 2410-2414.

Mallik, R. et al., Simulator Based CT: 4 Years of Experience at the Royal North Shore Hospital, Sydney, Australia, Apr. 1993, pp. 177-185.

Munro, P. et al., Megavoltage Cone-Beam Computed Tomography Using a High Quantum Efficiency Image Receptor, 2002, pp. 1340.

Munro, P. et al., A Digital Fluoroscopic Imaging Device for Radiotherapy Localization, 1990, pp. 641-649.

Munro, P., On Line Portal Imaging, 1997, pp. 114.

Ning, R. et al., Real Time Flat Panel Detector-Based Volume Tomographic Angiography Imaging: Detector Evaluation, Feb. 2000, pp. 396-407.

Munro, P. et al., Therapy imaging: limitations of imaging with high energy x-ray beams, 1987, pp. 178-184.

Wright, M. et al., Amorphous silicon dual mode medical imaging system, Feb. 1998, pp. 505-514.

Cho, Y. et al., Thermal Modelling of a Kilovoltage X-Ray Source for Portal Imaging, Jul. 2000, pp. 1856-1860.

Ebert, M. et al., 3D image guidance in radiotherapy: a feasibility study, 2001, pp. 1807-1816.

Ford, E.C. et al., Cone-beam CT with megavoltage beams and an amorphous silicon electronic portal imaging device: Potential for verification of radiotherapy of lung cancer, 2002, pp. 2913-2924.

Hunt, P. et al., Development of an IMRT quality assurance program using an amorphous silicon electronic portal imaging device, 2000, 1 page.

Mueller, K. et al., Cone-Beam Computed Tomography (CT) for a Megavoltage Linear Accelerator (LINAC) Using an Electronic Portal Imaging Device (EPID) and the Algebraic Reconstruction Technique (ART), Jul. 2000, pp. 2875-2878

Rowbottom, C. et al., Simultaneous optimization of beam orientations and beam weights in conformal radiotherapy, 2001, pp. 1696-1702.

Milliken B. et al., Verification of the omni wedge technique, 1998, pp. 1419-1423.

Mohan, R., Three Dimensional Dose Calculations for Radiation Treatment Planning, 1991, pp. 25-36.

Oldham M. et al., Practical aspects of in situ 16O (y,n) 15O activation using a conventional medical accelerator for the purpose of perfusion imaging, Aug. 2001, pp. 1669-1678.

Perera H. et al., Rapid Two-Dimensional Dose Measurement in Brachytherapy Using Plastic Scintillator Sheet: Linearity, Signal-to-Noise Ratio, and Energy Response Characteristics, 1992, pp. 1059-1069.

Purdy J. et al., State of the Art of High Energy Photon Treatment Planning, 1987, pp. 4-24.

Sharpe M. et al., Compensation of x-ray beam penumbra in conformal radiotherapy, Aug. 2000, pp. 1739-1745.

Sharpe M. et al., Monitor unit settings for intensity modulated beams delivered using a step- and-shoot approach, Dec. 2000, pp. 2719-2725.

Shiu A et al., Verification data for electron beam dose algorithms, 1992, pp. 623-636.

Sontag M. et al., State-of-the-Art of External Photon Beam Radiation Treatment Planning, 1991, pp. 9-23.

Stromberg J. et al., Active Breathing Control (ABC) for Hodgkin's Disease: Reduction in Normal Tissue Irradiation with Deep Inspiration and Implications for Treatment, 2000, pp. 797-806.

Teicher B. et al., Allosteric effectors of hemoglobin as modulators of chemotherapy and radiation therapy in vitro and in vivo, 1998, pp. 24-30.

Tepper J. et al., Three-Dimensional Display in Planning Radiation Therapy: A Clinical Perspective, 1991, pp. 79-89.

Urie M. et al., The Role of Uncertainty Analysis in Treatment Planning, 1991, pp. 91-107.

Vicini F. et al., Dose-Volume Analysis for Quality Assurance of Interstitial Brachytherapy for Breast Cancer, 1999, pp. 803-810.

Vicini F. et al., Implementation of 3D-Virtual Brachytherapy in the Management of Breast Cancer: A Description of a New Method of Interstitial Brachytherapy, 1998, pp. 629-635.

Vicini F. et al., Low-Dose-Rate Brachytherapy as the Sole Radiation Modality in the Management of Patients with Early-Stage Breast Cancer Treated with Breast-Conserving Therapy: Preliminary Results of a Pilot Trial, 1997, pp. 301-310.

Williamson J. et al., One-dimensional scatter-subtraction method for brachytherapy dose calculation near bounded heterogeneities, 1993, pp. 233-244.

Wong J. et al., Conservative management of osteoradionecrosis, Jul. 1997, pp. 16-21.

Wong J. et al., The Cumulative Verification Image Analysis Tool for Offline Evaluation of Portal Images, 1995, pp. 1301-1310.

Wong J. et al., Development of a Second-Generation Fiber-Optic On-Line Image Verification System Effect of small Inhomogeneities on dose in a cobalt-60 beam, 1993, pp. 311-320.

Wong J. et al., Effect of small Inhomogeneities on does in a cobalt-60 beam, 1981, pp. 783-791.

Wong J. et al., On methods of inhomogeneity corrections for photon transport, 1990, pp. 807-814.

Wong J. et al., A new approach to CT pixel-based photon dose calculations in heterogeneous media, 1983, pp. 199-208.

Wong J. et al., On-line image verification in radiation therapy: an early USA experience, 1993, pp. 43-54.

Wong J. et al., On-line Readiotherapy Imaging with an Array of Fiber-Optic Image Reducers, 1990, pp. 1477-1484.

Wong J. et al., Portal Dose Images I: Quantitative Treatment Plan Verification, 1990, pp. 1455-1463.

Wong J. et al., Reconsideration of the power-law (Batho) equation for inhomogeneity corrections, 1982, pp. 521-530.

Wong J. et al., Role of Inhomogeneity Corrections in Three-Dimensional Photon Treatment Planning, 1991, pp. 59-69.

Wong J. et al., Second scatter contribution to dose in a cobalt-60 beam, 1981, pp. 775-782.

Wong J. et al., Treatment Verifications and Patient Dose Estimations Using Portal Dose Imaging, 1988, pp. 213-225.

Wong J. et al., The Use of Active Breathing Control (ABC) to Reduce Margin for Breathing Motion, 1999, pp. 911-919.

Wu Y. et al., Implementing multiple static field delivery for intensity modulated beams, Nov. 2001, pp. 2188-2197.

Yan D. et al., The influence of Interpatient and Intrapatient Rectum Variation on External Beam Treatment of Prostate Cancer, 2001, pp. 1111-1119.

Yan D. et al., A Model to Accumulate Fractionated Dose in a Deforming Organ, 1999, pp. 665-675.

Yan D. et al., A New Model for "Accept or Reject" Strategies in Off-Line and On-Line Megavoltage Treatment Evaluation, 1995, pp. 943-952.

Ying X. et al., Portal Dose Images II: Patient Dose Estimation, 1990, pp. 1465-1475.

Yu C. et al., A method for implementing dynamic photon beam intensity modulation using independent jaws and a multileaf collimator, 1995, pp. 769-787.

Ying X. et al., A multiray model for calculating electron pencil beam distribution, 1988, pp. 662-671.

Ying X. et al., Photon dose perturbations due to small inhomogeneities, 1987, pp. 78-83.

Yu C. et al., Photon does calculation incorporating explicit electron transport, Jul. 1995, pp. 1157-1166.

MDS Nordion, Advanced Workstation for Irregular Field Simulation and Image Matching, 1999, 7 pages.

Bortfeld et al., Clinically relevant intensity modulation optimization using physical criteria, 1997, pp. 1-4.

Brewster et al., Automatic generation of beam apertures, 1993, pp. 1337-1342.

Yu C. X., Intensity-modulated arc therapy with dynamic multileaf collimation: An alternative to tomotherapy[1], 1995, pp. 1435-1449.

Cho, Paul S. et al., Cone-Beam CT for Radiotherapy Applications, 1995, pp. 1863-1883.

Chui, C.S. et al., Dose calculation for photon beams with intensity modulation generated by dynamic jaw or multileaf collimations, 1994, pp. 1237-1244.

(56) References Cited

OTHER PUBLICATIONS

I.M.R.T.C.W. Group, Intensity-modulated radiotherapy: Current status and issues of interest, 2001, pp. 880-914.
Keys, D. et al., A CCTV-Microcomputer Biostereometric System for Use in Radiation Therapy (Topography, Medical Physics, Tissue Compensators), 1984, pp. 3857.
Kirkpatrick, S. et al., Optimization by simulated annealing, 1983, pp. 671-680.
Kudo et al., Feasible Cone Beam Scanning Methods for Exact Reconstruction in Three-Dimensional Tomography, 1990, pp. 2169.
Wu, Q. et al., Dynamic splitting of large intensity-modulated fields, Jul. 2000, pp. 1731-1740.
Verfaillie, G. et al., Russian Doll Search for Solving Constraints Optimization Problems, 1996, pp. 181-187.
Carey, G. F., Computational Grids: Generations, Adaptation & Solution Strategies, 1997.
van Herk et al., Automatic three-dimensional correlation of CT-CT, CT-MRI, and CT-SPECT using chamfer matching, Medical Physics 21(7), Jul. 1994, pp. 1163-1178.
Woods et al., MRI-PET Registration with Automated Algorithm, Journal of Computer Assisted Tomography 17(4), Jul./Aug. 1993, pp. 536-546.
L. Antonuk, Electronic portal imaging devices: a review and historical perspective of contemporary technologies and research, Mar. 1, 2002, pp. R31-R65.
Shirazi et al., A cone-beam megavoltage CT scanner for treatment verification in conformal radiotherapy, 1998, pp. 319-328.
Agostinelli, S. et al., A prototype 3D CT extension for radiotherapy simulators, 2001, pp. 11-21.
Cho et al., Digital radiotherapy simulator, 1998, pp. 1-7.
Hartson, M. et al., Comparison of CT numbers determined by a simulator CT & a diagnostic scanner, 1995, pp. 37-45.
Yu, C., Intensity Modulated Arc Therapy: Technology and Clinical Implementation, Sep. 1995, pp. 1-14.
Chin et al., Dose Optimization with Computer-Controlled Gantry Rotation, Collimator Motion and Dose-Rate Variation, May 1983, pp. 723-729.
Cotrutz et al., Intensity modulated arc therapy (IMAT) with centrally blocked rotational fields, 2000, pp. 2185-2206.
Yu, C. Intensity-modulated arc therapy with dynamic multileaf collimation: an alternative to tomotherapy, 1995, pp. 1435-1449.
Nakagawa T. et al., Accuracy improvement of irradiation position and new trend, 2001, pp. 102-105.
Nishiki M., X-ray detector in IT era-FPD: Flat Panel Detector, 2001, pp. 1-2.
Watanabe, Y., Development of corn beam X-ray CT system, Oct. 2002, pp. 778-783.
The Stanford medical linear accelerator. II. Installation and physical measurements, 1959, Weissbluth, M., C. J., Karzmark et al., 242-253.
Akanuma, A., et al., New Patient Set Up in Linac-CT Radiotherapy System—First Mention of a Hybrid CT-Linac System, 1984, pp. 465-467.
Schewe, J. E. et al., A room-based diagnostic imaging system for measurement of patient setup, Dec. 1998, pp. 2385-2387.
Antonuk L. et al., Strategies to improve the signal and noise performance of active matrix, flat-panel imagers for diagnostic x-ray applications, Feb. 2000, pp. 289-306.
Bassett P., An Interactive Computer System for Studying Human Mucociliary Clearance, 1979, pp. 97-105.
Bissonnette J. et al., Optimal radiographic magnification for portal imaging, Sep. 1994, pp. 1435-1445.
Boyer A. et al., Intensity-Modulated Radiotherapy: Current Status and Issues of Interest, 2001, pp. 880-914.
Brown A. et al., Three-Dimensional Photon Treatment Planning for Hodgkin's Disease, May 1992, pp. 205-215.
Cheng A. et al., Systematic verification of a three-dimensional electron beam dose calculation algorithm, 1996, pp. 685-693.
Cullity B., Elements of X-Ray Diffraction, 1978, pp. 6-12.
Dieu L. et al., Ion Beam Sputter-Deposited SiN/TiN Attenuating Phase-Shift Photoblanks, 2001, pp. 810-817.
Du M. et al., A Multileaf Collimator Field Prescription Preparation System for Conventional Radiotherapy, 1994, pp. 707-714.
Du M. et al., A Multileaf Collimator Field Prescription Preparation System for Conventional Radiotherapy, 1995, pp. 513-520.
El-Mohri Y. et al., Relative dosimetry using active matrix flat-panel imager (AMFPI) technology, 1999, pp. 1530-1541.
Frazier A. et al., Dosimetric Evaluation of the Conformation of the Multileaf Collimator to Irregularly Shaped Fields, 1995, pp. 1229-1238.
Frazier A. et al., Effects of Treatment Setup Variation on Beam's Eye View Dosimetry for Radiation Therapy Using the Multileaf Collimator vs. the Cerrobend Block, 1995, pp. 1247-1256.
Graham M. et al., A Method to Analyze 2-Dimensional Daily Radiotherapy Portal Images from an On-Line Fiber-Optic Imaging System, 1991, pp. 613-619.
Halverson K. et al., Study of Treatment Variation in the Radiotherapy of Head and Neck Tumors Using a Fiber-Optic On-Line Radiotherapy Imaging System, 1991, pp. 1327-1336.
Harms W. et al., A software tool for the quatitative evaluation of 3D dose calculation algorithms, 1998, pp. 1830-1836.
Jaffray D. et al., Activity distribution of a cobalt-60 teletherapy source, 1991, pp. 288-291.
Jaffray D. et al., Conebeam Tomographic Guidance of Radiation Field Placement for Radiotherapy of the Prostate, 1998, pp. 1-32.
Jaffray D. et al., X-ray scatter in megavoltage transmission radiography: Physical characteristics and influence on image quality, Jan. 1994, pp. 45-60.
Jaffray D. et al., X-ray sources of medical linear accelerators: Focal and extra-focal radiation, 1993, pp. 1417-1427.
Kestin L. et al., Improving the Dosimetric Coverage of Interstitial High-Dose-Rate Breast Implants, 2000, pp. 35-43.
Kestin L. et al., Intensity Modulation to Improve Dose Uniformity With Tangential Breast Radiotherapy: Initial Clinical Experience, 2000, pp. 1559-1568.
Kini V. et al., Use of Three-Dimensional Radiation Therapy Planning Tools and Intraoperative Ultrasound to Evaluate High Dose Rate Prostate Brachytherapy Implants, 1999, pp. 571-578.
Laughlin J. et al., Evaluation of High Energy Photon External Beam Treatment Planning: Project Summary, 1991, pp. 3-8.
Lockman et al., Estimating the dose variation in a volume of interest with explicit consideration of patient geometric variation, Sep. 2000, pp. 2100-2108.
Martinez A. et al., Improvement in Dose Escalation Using the Process of Adaptive Radiotherapy Combined with Three-Dimensional Conformal or Intensity-Modulated Beams for Prostate Cancer, 2001, pp. 1226-1234.
Masterson M. et al., Interinstitutional Experience in Verification of External Photon Dose Calculations, 1991, pp. 37-58.
Michalski J. et al., An Evaluation of Two Methods of Anatomical Alignment of Radiotherapy Portal Images, 1993, pp. 1199-1206.
Michalski J. et al, Prospective Clinical Evaluation of an Electronic Portal Imaging Device, 1996, pp. 943-951.
Michalski J. et al., The Use of On-line Image Verification to Estimate the Variation in Radiation Therapy Dose Delivery, 1993, pp. 707-716.

\* cited by examiner

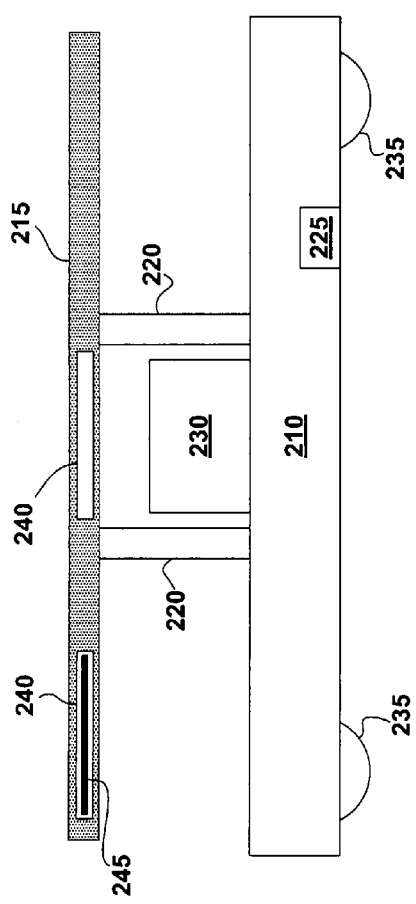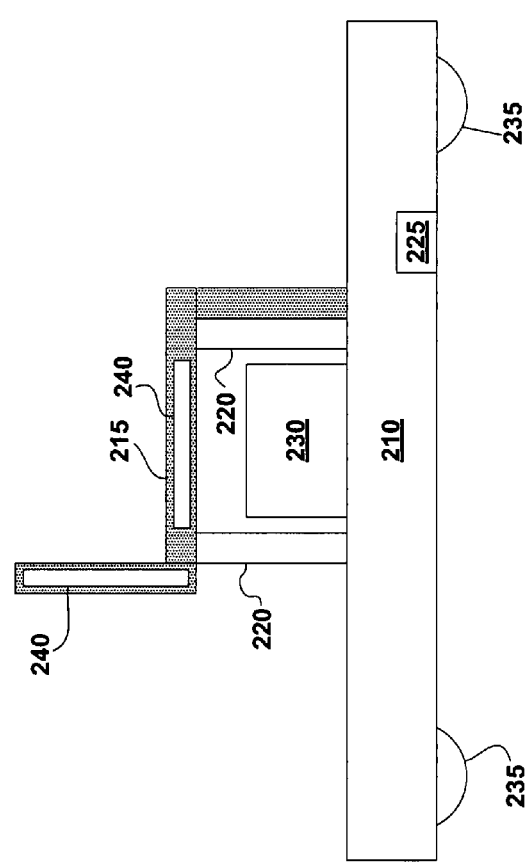

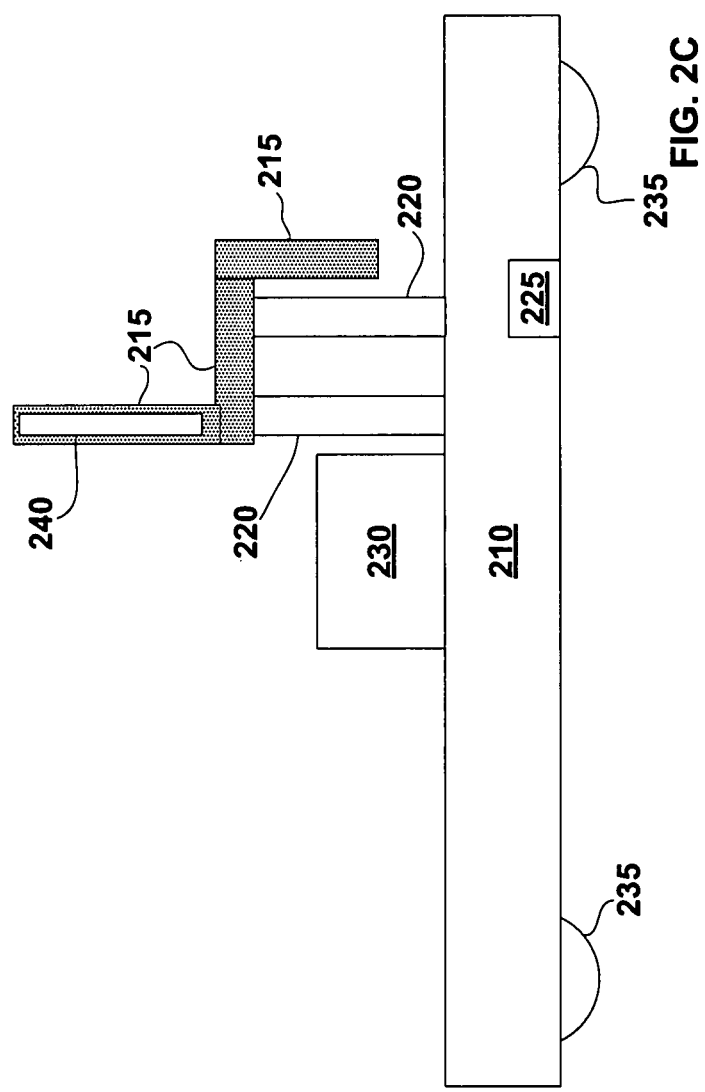

DYNAMIC PATIENT POSITIONING SYSTEM

CROSS-REFERENCE TO RELATED APPLICATIONS

This application claims benefit of U.S. Provisional Patent Application 60/859,675 filed Nov. 17, 2006 and entitled "Dynamic Patient Positioning System";

this application is also a continuation-in-part of U.S. patent application Ser. No. 11/415,974 filed May 1, 2006 now U.S. Pat. No. 7,640,607 and entitled "Patient Support Systems" which in turn claims benefit of U.S. Provisional Patent Application 60/676,138 filed Apr. 29, 2005 and entitled "Radiation Systems, Components Thereof, and Methods of Using the Same";

this application is also a continuation-in-part of U.S. patent application Ser. No. 11/447,532 filed Jun. 5, 2006 now U.S. Pat. No. 7,547,901 and entitled "Multiple Beam Path Particle Source";

this application is related to U.S. patent application Ser. No. 11/415,957, filed May 1, 2006 and entitled "Systems and Methods for Treating Patients Using Radiation"; U.S. patent application Ser. No. 11/415,866, filed May 1, 2006 and entitled "Radiation Systems"; and U.S. patent application Ser. No. 11/415,965, filed May 1, 2006 and entitled "Radiation Systems with Imaging Capability."

The disclosures of the above patent applications are hereby incorporated herein by reference.

BACKGROUND

1. Field of the Invention

The invention is in the field of radiation therapy and more specifically in the field of positioning a patient relative to a therapeutic beam.

2. Related Art

Mechanical and motor powered systems for transporting patients for radiation therapy are known in the art. These systems are typically configured to transport a patient from a preparatory location to a predetermined treatment location. At the treatment location, a second device may then used to position a patient relative to a treatment beam. Precise and accurate positioning of the patient relative to the treatment beam is important because treatment outcome depends, in part, on overlap between a part of a patient to be exposed to the beneficial effects of the radiation, referred to herein as a treatment volume, and the treatment beam. Patient positioning is typically performed under manual control and, thus, can require significant time and effort. This time and effort may significantly limit the number of patients that can be treated by a treatment system.

SUMMARY

Various embodiments of the invention include systems and methods of moving one or more patients from a preparation area to one or more treatment areas. One or more devices configured to transport patients is optionally further configured to position patients relative to one or more treatment beams after arrival at a treatment area. These systems are optionally further configured to position patients in a variety of different positions. For example, a transport system may be alternatively used to position a patient in a supine or sitting position.

Various embodiments of the invention include a control system configured to manage transport and/or positioning of patients. This control system may, for example, be configured to transport a patient along a variety of alternative transport paths to a variety of alternative treatment stations. Operation of the control system is optionally responsive to information regarding identity of a patient and a treatment plan associated with the patient.

Various embodiments include a treatment system comprising a particle beam source configured to generate a therapeutic beam of particles, a particle beam nozzle to direct the therapeutic beam of particles in a first treatment area, and an automated patient transport configured to transport a patient from a preparation area to the first treatment area and to position a treatment volume within the patient relative to the therapeutic beam of particles, the automated patient transport including a position sensor configured for use in determining the relative positions of the treatment volume and the therapeutic beam of particles.

Various embodiments include a treatment system comprising a particle beam source configured to generate a beam of particles, a particle beam nozzle to direct the beam of particles in a first treatment area, and a patient transport system configured for moving a plurality of patients from a preparation area to the first treatment area, the patient transport system including a first automated patient transporter configured to transport a first of the plurality of patients in a sitting position and a second automated patient transporter configured to transport a second of the plurality of patients in a supine position.

Various embodiments include a treatment system comprising a particle beam source configured to generate a beam of particles, a plurality of particle beam paths configured to direct the beam of particles to a plurality of treatment areas, an automated patient transport configured to transport a first patient to a first of the plurality of treatment areas along a first transport path and to transport a second patient to a second of the plurality of treatment areas along a second transport path, and logic configured to select between the first transport path and the second transport path.

Various embodiments include a treatment system comprising a patient database configured to store a patient identity, a particle beam source configured to generate a beam of particles, a plurality of particle beam paths configured to alternatively direct the particles to a plurality of treatment areas, a patient transporter configured to transport a patient from a preparation area to a selected one of the plurality of treatment areas, for treatment using the particles, and a control system configured to receive the patient identity, access a patient treatment plan responsive to the patient identity, direct the patient transporter to move the patient to the selected one of the plurality of treatment areas responsive to the patient treatment plan, and position a treatment volume within the patient relative to the particles according to the treatment plan.

Various embodiments include a patient transporter comprising a transport section including a drive system configured to propel the patient transporter, a first patient support configured to hold a patient in a sitting position while the patient transporter is propelled using the transport section, a second patient support configured to hold a patient in a supine position while the patient transporter is propelled using the transport section, and a mount configured to alternatively couple the first patient support or the second patient support to the transport section.

Various embodiments include a system comprising logic configured to receive an identity of a patient, logic configured to access a patient treatment plan from a patient database responsive to the identity of the patient, logic configured to direct a patient transporter to transport the patient to a selected one of a plurality of alternative treatment areas responsive to the patient treatment plan, logic configured to position the patient relative to a beam of therapeutic particles within the selected one of a plurality of alternative treatment areas, and logic configured to use a particle beam source to deliver the beam of therapeutic particles to a treatment volume within the patient according to the patient treatment plan.

Various embodiments include a method comprising generating position information by detecting a position of a treatment volume of a patient relative to a position sensor of an automated patient transporter, transporting the patient from a preparation area to a treatment area using the automated patient transporter, the preparation area being protected from radiation at the treatment area, determining a position of the automated patient transporter within the treatment area using the position sensor, and positioning the treatment volume relative to a treatment beam disposed within the treatment area, using the automated patient transporter, a position of the treatment volume relative to the treatment beam being determined using the position information.

Various embodiments include a treatment system comprising a radiation source configured to generate a therapeutic beam of radiation, a treatment head to direct the therapeutic beam of radiation in a first treatment area, and an automated patient transport configured to transport a patient from a preparation area to the first treatment area and to position a treatment volume within the patient relative to the therapeutic beam of radiation, the automated patient transport including a position sensor configured for use in determining the relative positions of the treatment volume and the therapeutic beam of radiation.

BRIEF DESCRIPTION OF THE DRAWINGS

FIGS. 2A-2C illustrate various embodiments of a multi-position automated patient transporter;

DETAILED DESCRIPTION

A patient treatment system includes an automated patient transporter configured to transport a patient from a preparation area to a treatment area. In some embodiments the automated patient transporter is configured to both transport the patient to the treatment area and to finely position the patient relative to a treatment beam after arriving at the treatment area. Typically, the preparation area is separate and/or shielded from the treatment area such that a first patient can be prepared in the preparation area while a second patient receives treatment in the treatment area. In some embodiments, the automated patient transporter is configured to transport a patient to one of a number of alternative treatment areas. For example, an automated patient transporter can be programmed to transport the patient to a specific treatment area responsive to a patient treatment plan or a treatment schedule.

Figure 1:
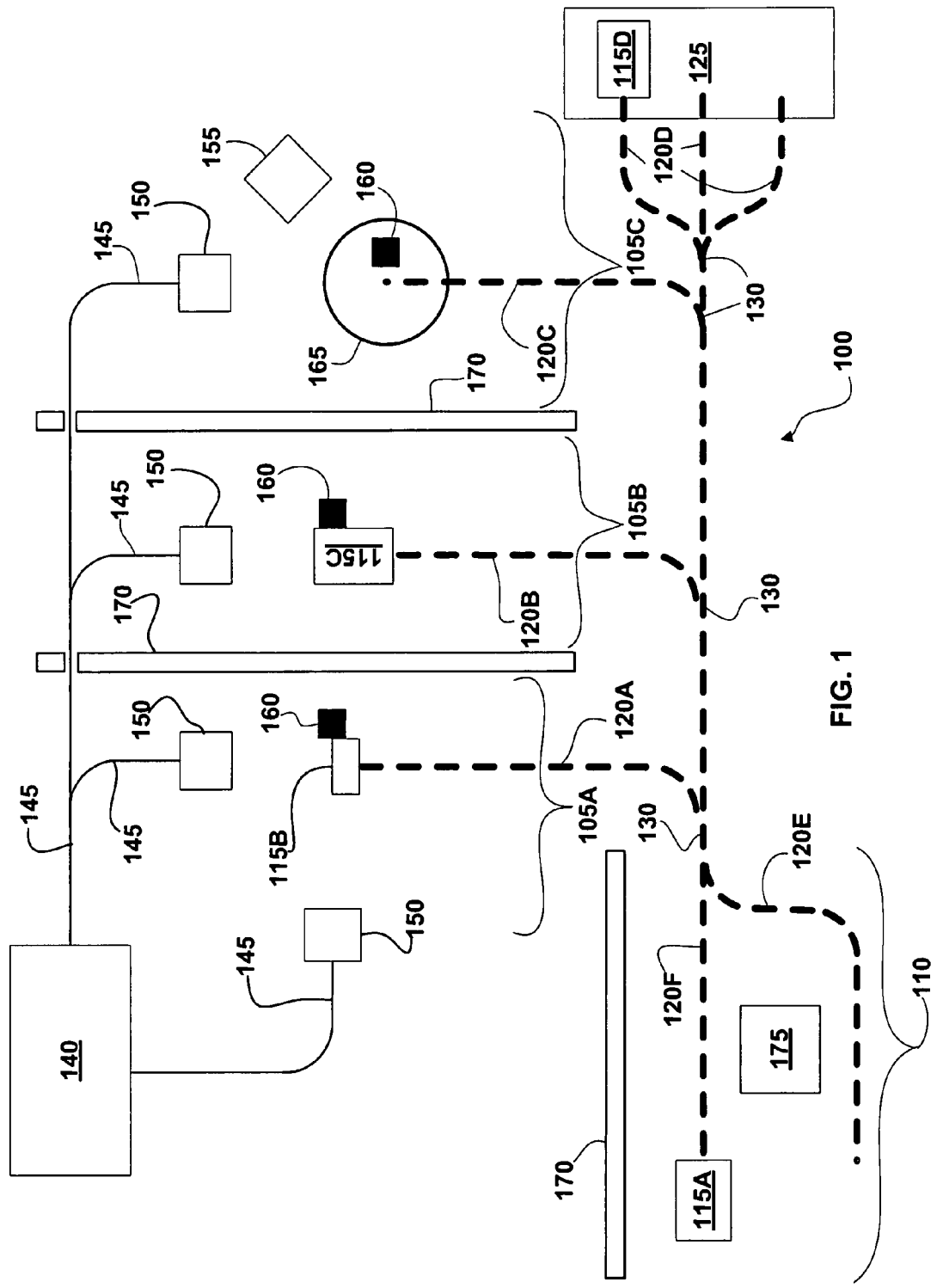
FIG. 1 illustrates various embodiments of a treatment system.

FIG. 1 illustrates a Treatment System, generally designated 100. In various embodiments, Treatment System 100 includes one, two or more Treatment Areas 105 (individually designated 105A-105C) and a Preparation Area 110. Preparation Area 110 is configured for preparing one or more patients for treatment. For example, in Preparation Area 110, a patient may be positioned and stabilized on one of several Automated Patient Transporters 115, (individually designated 115A-115D). As is further described herein, this positioning typically includes determining a position of a desired treatment volume within the patient relative to the Automated Patient Transporter 115A-115D. Various embodiments include one, two, three or more of Automated Patient Transporter 115.

Treatment System 100 optionally further includes one or more alternative Transport Paths 120 (individually designated 120A-120F). Transport Paths 120 are configured for use by Automated Patient Transporters 115 in order to travel between Preparation Area 110, Treatment Areas 105, and an optional Storage Area 125. In some embodiments, Transport Paths 120 include one or more Switches 130 and one, two or more rails on which Automated Patient Transporters 115 move. In various embodiments, Transport Paths 120 include magnetic, electrical, or electromagnetic markers, or preprogrammed data representative of a route. For example, Transport Paths 120 may include an under-floor wire configured to emit a signal that Automated Patient Transporters 115 can follow. Transport Paths 120 may include data stored on computer readable media within Automated Patient Transporters 115 and configured to reproducibly guide Automated Patient Transporters 115 along selected Transport Paths 120.

Typically, at least one of Transport Paths 120 is configured for transporting a patient to each of the Treatment Areas 105. Preparation Area 110 can include one, two or more different Transport Paths 120. More than one of these Transport Paths 120 within Preparation Area 110 may be used for the preparation of more than one patient at a time or preparation of one patient on one of Automated Patient Transporters 115 while a second patient is being removed from a second of Automated Patient Transporters 115.

Storage Area 125 is configured to store one or more Automated Patient Transporters 115 when the one or more Automated Patient Transporters 115 is not in use. Storage Area 125 optionally includes a charging station (not shown) configured for charging a power source within Automated Patient Transporters 115.

Treatment System 100 further includes a radiation source configured to generate one or more treatment beams configured for therapeutic use. In embodiments illustrated by FIG. 1, the radiation source includes a Particle Beam Generator 140 configured to generate a beam of high energy particles, e.g., particles with energies greater than 5, 10, 20, 50, 70, 100, 250 or 500 MeV. These particles may include hydrogen, carbon, neutrons, electrons, ions, neutrals, and/or the like, and are directed along one or more Beam Paths 145 to Particle Beam Sources 150. In various embodiments, Particle Beam Generator 140, Beam Paths 145 and/or Particle Beam Sources 150 (and associated particle beam nozzles) include systems described in U.S. patent application Ser. No. 11/447,532. In various embodiments, each of Treatment Areas 150 alternatively or further includes other types of radiation sources such as x-ray sources.

Some Treatment Areas 105 optionally include more than one Particle Beam Source 150. For example, Treatment Area 105A includes two Particle Beam Sources 150. Automated Patient Transporters 115 are optionally configured to position a patient relative to either and/or both of these two Particle Beam Sources 150. Some Treatment Areas 105 optionally include both Particle Beam Source 150 and an X-ray Source 155. X-ray Source 155 optionally includes systems described in U.S. patent application Ser. No. 11/415,974. X-ray Source 155 is configured for imaging and/or treatment of a patient. For example, in some embodiments, X-ray Source 155 is configured for imaging a treatment volume within a patient and Particle Beam Source 150 is configured for generation of a particle beam for radiation of the treatment volume. Automated Patient Transporter 115 may be configured to adjust the position of the patient in response to data generated using X-ray source 115 such that the treatment volume is intersected in a desirable manner by the particle beam.

Typically, Treatment Area 105 further includes one or more Area Position Sensors 160. Area Position Sensor 160 is configured for use in detecting positions of Automated Patient Transporter 115 within Treatment Area 105. For example, in some embodiments, Area Position Sensor 160 includes an encoder configured to read a marking on Automated Patient Transporter 115C. Alternatively, Area Position Sensor 160 may include a marking configured to be read by an encoder on Automated Patient Transporter 115C.

In various embodiments, Area Position Sensor 160 includes a docking device configured to mechanically couple with Automated Patient Transporter 115. For example, Area Position Sensor 160 may include a locator pin, clamp, pin receiver, three point kinamatic coupling, rail, slot, electrical contact, or the like, configured to engage and precisely establish a position of one or more Automated Patient Transporters 115. In some embodiments, Area Position Sensor 160 includes radiofrequency or optical devices configured for position detection. For example, Area Position Sensor 160 may include a radio frequency identification tag or tag sensor, part of an optical interferometer, a radio frequency positioning system element, or the like.

Area Position Sensor 160 is configured such that the position of one of Automated Patient Transporters 115 can be precisely detected relative to a radiation source such as one of Particle Beam Sources 150, X-ray Source 155, or an x-ray or particle beam generated thereby. In various embodiments, the precision of this detection is less than or equal to +/−3, 2, 1.5, 1, 0.5, 0.25, or 0.1 millimeters. As is described further herein, the detected position can be used in combination with information relating the relative positions of a treatment volume and an Automated Patient Transporter 115 to determine a positional relationship between the treatment volume and treatment beam.

One or more Treatment Areas 105 optionally include a Turntable 165 configured to rotate Automated Patient Transporters 115 around one or more pivot points. For example, Turntable 165 may be configured to alternatively receive Automated Patient Transporter 115A and/or 115B, via Transport Path 120C, and then rotate the received Automated Patient Transporter 115 around a vertical and/or horizontal axis. In some embodiments, Turntable 165 is configured to rotate Automated Patient Transporter 115 such that a patient is positioned relative to different radiation sources. These different radiation sources can include a particle beam source and an x-ray source, two particle beam sources, and/or two x-ray sources. For example, Turntable 165 may be configured such that a patient is first positioned relative to X-ray Source 155, where imaging information can be generated. Turntable 165 is then used to rotate the Automated Patient Transporter 115 such that the patient is positioned relative to the Particle Beam Source 150 within Treatment Area 105C. As such, the patient can receive therapeutic radiation at the same relative angle as the imaging information was obtained.

Turntable 165 is optionally used to rotate Automated Patient Transporter 115 configured to transport a patient in a sitting, standing, and/or supine position. For example, in some embodiments, Turntable 165 is configured to rotate an embodiment of Automated Patient Transporter 115 configured to support a patient in a sitting position. In some embodiments, Turntable 165 is configured to rotate an embodiment of Automated Patient Transporter 115 configured to support a patient in a supine position. In some embodiments, Turntable 165 is configured to rotate an embodiment of Automated Patient Transporter 115 that is configured to support a patient in a variety of alternative positions.

In some embodiments, Turntable 165 is configured such that a patient can be positioned in a variety of positions relative to a particular Particle Beam Source 150. For example, a Particle Beam Source 150 configured to deliver a particle beam to a treatment volume through a horizontal plane may arrive at the treatment volume from a variety of different angles relative to a vertical axis by rotating the patient on Turntable 165. In some embodiments, this feature eliminates a need to have multiple Particle Beam Sources 150 at the same angle relative to the horizontal plane. For example, only one Particle Beam Source 150 is required at 45 degrees from the horizontal plane to direct a particle beam at a treatment volume from at position within a cone at 45 degrees rotated around an axis of rotation of Turntable 165. Likewise, only one Particle Beam Source 150 is required in the horizontal plane to direct a particle beam at the treatment volume from any angle within the horizontal plane.

Preparation Area 110 is typically protected from radiation at Treatment Areas 105. This protection can be achieved by distance or by one or more Barriers 170 including shielding. One or more Barriers 170 are also optionally configured to separate Treatment Areas 105. For example, Barriers 170 may be used to prevent radiation in Treatment Area 105A from reaching Treatment Area 105B in significant quantities.

Preparation Area 110 may also include all or part of a Control System 175. As is further described herein, Control System 175 is configured for controlling which Transport Paths 120 are used by which Automated Patient Transporters 115, controlling operation of radiation beams, identifying patients, accessing treatment plans, and/or the like. Alternatively, all or part of Control System 175 is optionally located somewhere other than Preparation Area 110.

Preparation Area 110 may comprise one or more physically or visually separate areas or rooms made separate via any known means such as curtains, dividers, partitions, walls, floors, etc.

FIGS. 2A-2C illustrate further details of Automated Patient Transporter 115, according to various embodiments. As illustrated in FIG. 2A, Automated Patient Transporter 115 includes a Transport Section 210 and a Patient Support 215, optionally separated by one or more Braces 220. Patient Support 215 is optionally configured to support a patient in one or more alternative positions. For example, FIG. 2A illustrates an embodiment of Patient Support 215 configured for supporting a patient in a supine position. As used herein, the term supine is intended to include lying on a side or stomach, in addition to lying on the back. FIG. 2B illustrates an embodiment of Patient Support 215 configured for supporting a patient in a sitting position. Patient Support 215 is optionally configured to bend or otherwise move in one or more locations such that the same Patient Support 215 can be adjusted into both of the configurations illustrated in FIGS. 2A and 2B.

In some embodiments, Patient Support 215 is removable from Transport Section 210. For example, the embodiment of Patient Support 215 illustrated in FIGS. 2A and 2B may be removed from Transport Section 210 and replaced with the embodiment of Patient Support illustrated in FIG. 2C. In this approach, Transport Section 210 may be used to transport patients in a variety of different positions by attaching different embodiments of Patient Support 215.

Patient Support 215, illustrated in FIGS. 2A-2C, optionally includes patient positioning indicators (not shown) configured to identify the position of a patient relative to Patient Support 215 and/or Transport Section 210. For example, Patient Support 210 may include surface markings indicative of patient positions. In some embodiments, Patient Support 215 includes an x-ray imaging detector. For example, Patient Support 215 may include one or more Receptacles 240 configured for receiving a removable X-ray Imaging Detector 245 configured for imaging a treatment volume within a patient.

Patient Support 215 typically includes elements configured to stabilize a patient. These elements may include a strap, clamp, pad, brace, collar, splint, and/or the like.

Transport Section 210 is configured to transport a patient, supported by Patient Support 215, between Preparation Area 110 and one or more of Treatment Areas 105. This transportation typically occurs along one or more predetermined Transport Paths 120. Transport Section 210 optionally includes Wheels 235 and may be configured to travel along one, two or more rails.

Movement of Transport Section 210 is optionally facilitated by a Driver/Logic 230. Driver/Logic 230 can include a motor, power source, microprocessor, memory, input/output interface, and/or the like. For example, in one embodiment, Driver/Logic 230 includes batteries, an electric motor configured to drive Wheels 235, memory configured to store characteristics of a selected member of Transport Paths 120, and a processor configured to control the electric motor and Wheels 235 such that Transport Section 210 travels along the selected member of Transport Paths 120.

Transport Section 210 and/or Patient Support 215 further include one or more Transporter Position Sensors 225. In some embodiments, Transporter Position Sensor 225 is configured to determine the position of Automated Patient Transporter 115 along Transport Paths 120. For example, if Transport Path 120 is marked using a guide wire embedded in a floor, then Transporter Position Sensor 225 may be configured to detect the guide wire. If Transport Path 120 includes a series of positions determined using radio frequency location signals, then Transporter Position Sensor 225 may be configured to detect these radio frequency location signals.

In some embodiments, Transporter Position Sensor 225 is configured to detect the position of Automated Patient Transporter 115 relative to Area Position Sensor 160. For example, Transporter Position Sensor 225 may include an encoder, an encoder pattern, an optical element, a wireless element, clamp, pin, pin receiver, mechanical device, and/or the like configured to interact with Area Position Sensor 160.

The two functions of detecting the position of an Automated Patient Transporter 115 along a Transport Path 120 and detecting the position of the Automated Patient Transporter 115 relative to Area Position Sensor 160 are optionally performed by separate parts of Transporter Position Sensor 225.

In some embodiments, the position of a treatment volume within a patient relative to a therapeutic radiation beam is detected by detecting the relative positions of the treatment volume and Transporter Position Sensor 225, the relative positions of Transporter Position Sensor 225 and Area Position Sensor 160, and the relative positions of Area Position Sensor 160 and the therapeutic radiation beam. The relative positions of the treatment volume and the Transporter Position Sensor 225 are optionally determined using X-ray Imaging Detector 245 inserted in Receptacle 240. For example, the relative positions of Receptacle 240 and Transporter Position Sensor 225 may be predetermined and an image received by X-ray Imaging Detector 245 may be used to detect the position of the treatment volume relative to the Receptacle 240.

In some embodiments, X-ray Source 155 is additionally or alternatively included in Preparation Area 110. In Preparation Area 110, X-ray Source 155 may be used to image the treatment volume and detect the position of the treatment volume relative to the Transporter Position Sensor 225 after the patient has been secured on Patient Support 215 but prior to transporting the patient to one of Treatment Areas 105. In some embodiments, X-ray Source 155, included in one of Treatment Areas 105, is additionally or alternatively used to detect the position of the treatment volume. X-ray Imaging Detector 245 may be removed from Receptacle 240 prior to treatment using a therapeutic particle beam. Other detector apparatus for detecting patient position may likewise be utilized including ultrasound imagers, radiofrequency detectors (e.g., for detecting radio signals affected by passive transmitters implanted in a patient, magnetic field detectors (e.g., for detecting small magnets implanted in a patient), etc.

Figure 3:
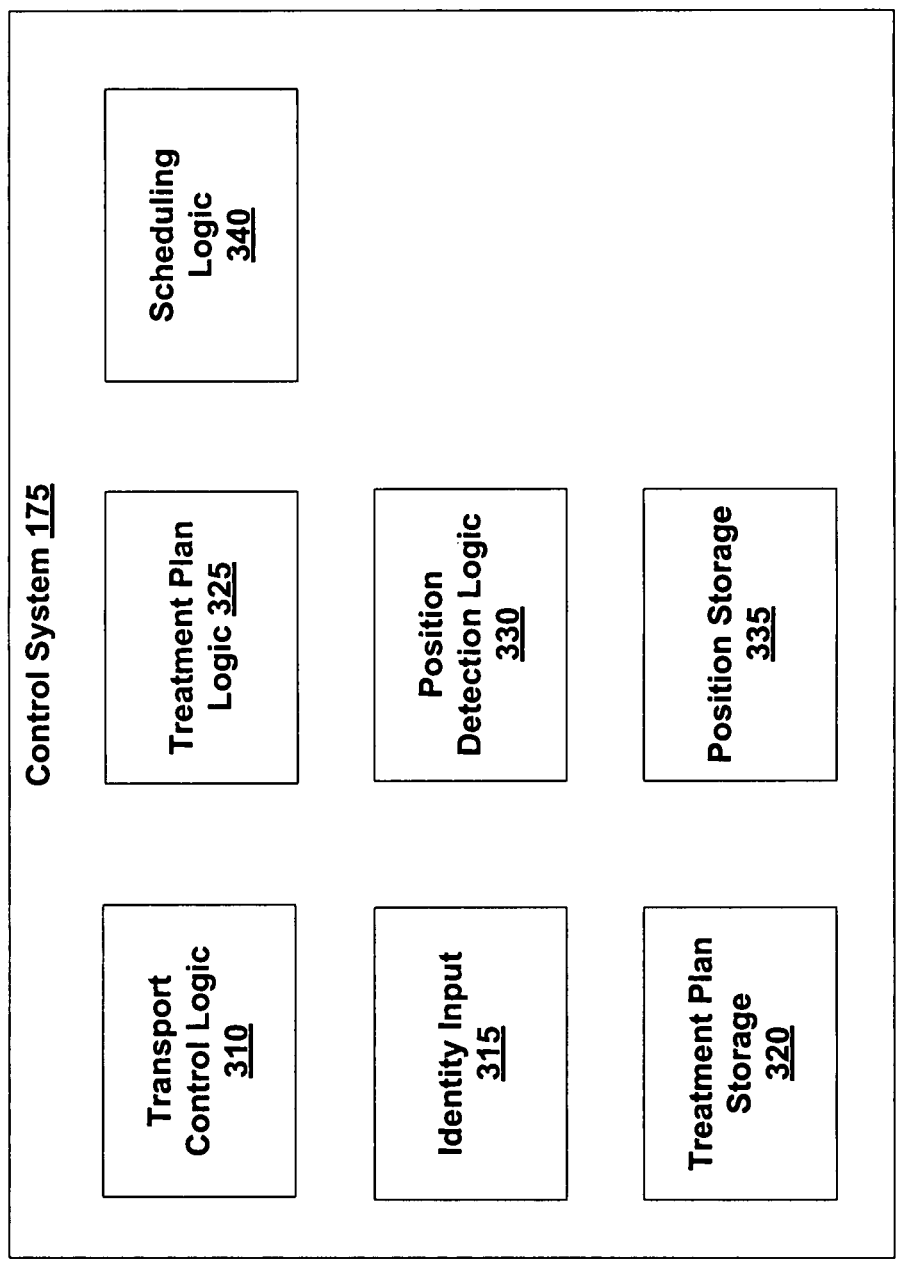
FIG. 3 illustrates various embodiments of a control system.

FIG. 3 illustrates various embodiments of Control System 175. These embodiments include a Transport Control Logic 310 configured to control the movement of Automated Patient Transporters 115 between Treatment Areas 105, Preparation Area 110 and/or Storage Area 125. For example, Transport Control Logic 310 is typically configured to identify a starting point and an ending point for patient transport. This identification may include determining a preferred path between these points. Transport Control Logic 310 may further be configured to control the fine positioning of a patient relative to a therapeutic radiation beam after the patient has been transported to one of Treatment Areas 105.

In various embodiments, Transport Control Logic 310 is configured to operate one or more of Switches 130 in Transport Paths 120, to send signals through a guide wire to guide one of Automated Patient Transporters 115 along one of Transport Paths 120, to start and stop movement of one of Automated Patient Transporters 115, and/or the like. Transport Control Logic 310 may also be configured for providing transport instructions to Drive/Logic 230, controlling movement of Turntable 165, controlling speeds of Automated Patient Transporters 115, and/or the like. Typically, Transport Control Logic 310 is configured to control movement of a plurality of Automated Patient Transporters 115 over a plurality of alternative Transport Paths 120. Finally, Transport Control Logic 310 is optionally configured for both controlling patient transport between Preparation Area 110 and one or more of Treatment Areas 105, as well as positioning of a treatment volume relative to a therapeutic radiation beam.

Transport Control Logic 310 is optionally distributed among a number of devices, some of which may be included in Automated Patient Transporters 115, Preparation Area 110 and/or Treatment Areas 105. In various embodiments, Transport Control Logic 310, as with other logic discussed herein, includes hardware, firmware, and/or software on a computer readable medium.

Control System 175 optionally further includes an Identity Input 315, Treatment Plan Storage 320, Treatment Plan Logic 325, Position Detection Logic 330, Position Storage 335, and/or Scheduling Logic 340.

Identity Input 315 is configured for receiving an identity of a patient. For example, Identity Input 315 may include a keypad, graphical user interface, a barcode reader, a radio frequency identification tag reader, a smartcard reader, and/or the like. A patient identity received using Identity Input 315 may be used to access a patient treatment plan characterizing radiation treatment to be received by the patient. This patient treatment plan may include, for example, a location of a treatment volume, a dosage, spatial distribution, depth distribution, and/or type of radiation. The patient treatment plan may also include use of a particular Treatment Area 105, Particle Beam Source 150, X-ray Source 155, and/or type of Patient Support 215 (e.g., a type to support the patient in a sitting or supine position).

The patient treatment plan is optionally stored in a Treatment Plan Storage 320 including a computer readable medium. For example, Treatment Plan Storage 320 may include computer memory, magnetic storage, optical storage, and/or a processor configured for executing a database application. In some embodiments, Treatment Plan Storage 320 is accessed using a patient database and includes further information about patients in addition to a particular treatment plan. Treatment Plan Storage 320 may, thus, be part of an information system located external to Preparation Area 110 or Treatment Areas 105. Alternatively, the patient treatment plan may be entered via Identity Input 315.

In some embodiments, a patient treatment plan is used by Treatment Plan Logic 20 to determine which Patient Support 215 and which of Automated Patient Transporters 115 should be used to transport a patient, as well as which of a plurality of alternative Treatment Areas 105 the patient should be transported to. The patient treatment plan may also be used to control operation of Particle Beam Generator 140, Particle Beam Sources 150, particle beam nozzles (not shown) associated with the Particle Beam Sources 150, and/or X-ray Source 155.

Position Detection Logic 330 is configured to detect a relative position between a treatment volume and Transporter Position Sensor 225. For example, in some embodiments Position Detection Logic 330 is configured to receive image data from an x-ray imaging detector and an indication of a treatment volume within the image data from a user, and to determine the position of the treatment volume relative to Transporter Position Sensor 225 using this information. In some embodiments, Position Detection Logic 330 is configured to receive information regarding a patient's position according to markings on Patient Support 215. For example, a technician may stabilize a patient on Patient Support 215 and then enter information about the patient's position based on markings on the Patient Support 215. In some embodiments, Position Detection Logic 330 is configured to detect markers located within or on the patient, e.g. an RFID tag, and determine the position of the treatment volume relative to Transporter Position Sensor 225 based on the location of these markers.

The position of the treatment volume relative to Transporter Position Sensor 225 is stored in Position Storage 335. Position Storage 335 typically includes a computer readable medium such as a hard drive, integrated circuit based memory cells, an optical drive, a magnetic drive, and/or the like. In some embodiments, Position Storage 335 is disposed external to Control System 175, for example in an external database or in Drive/Logic 230.

Scheduling Logic 340 is configured to schedule the use of Automated Patient Transporters 115, Treatment Areas 105, Preparation Area 110, Particle Beam Sources 150, particle beam nozzles, and/or the like. For example, in some embodiments, Scheduling Logic 340 is configured to optimize the use of each Treatment Area 105 by indicating the order and/or timing of each patient preparation in Preparation Area 110, directing Transport Control Logic 310 to transport patients to Treatment Areas 105, and/or activating Particle Beam Generator 140 as necessary for patient treatment. Scheduling Logic 340 is optionally configured to direct the preparation of one or more patients while one or more other patients are receiving radiation therapy.

Figure 4:
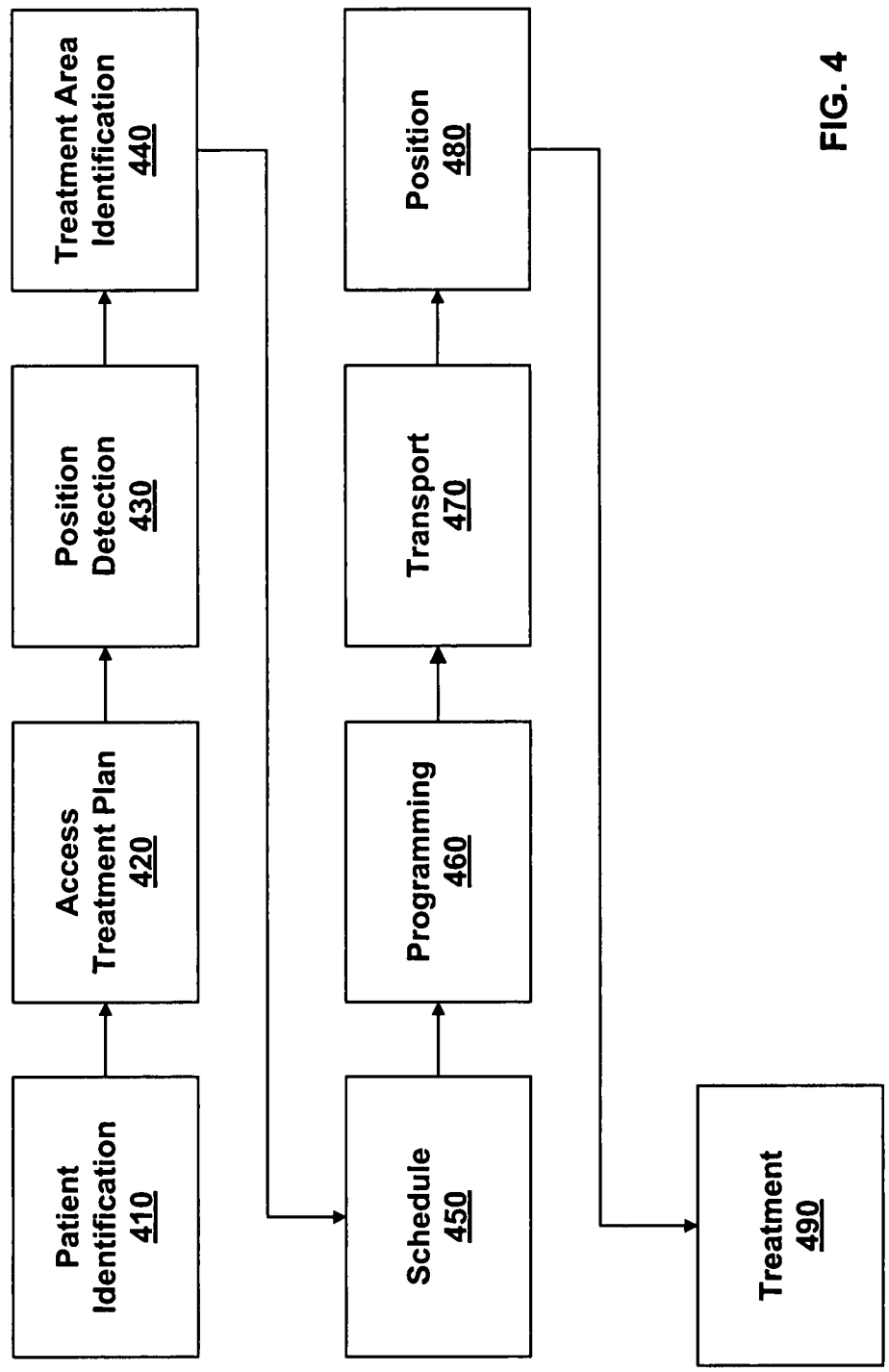
FIG. 4 illustrates various embodiments of a method of transporting a patient to a treatment area and treating the patient.

FIG. 4 illustrates a method of transporting a patient to a Treatment Area 105 and treating the patient. In this method a patient is identified, information about their planned treatment is accessed, and they are transported to a Treatment Area 105 where they receive treatment using therapeutic radiation.

In an optional Patient Identification Step 410, Identity Input 315 is used to identify a patient to receive therapeutic radiation. The patient may be identified using, for example, a barcode reader, an RFID tag reader, entering a name and/or identification number of the patient into a user interface, and/or the like.

In an optional Access Treatment Plan Step 420, the identity of a patient identified in Patient Identification step 410 is used to access a patient treatment plan optionally stored in Treatment Plan Storage 325. The identity of the patient may include an identification number, name, birth date, social security number, and/or the like, and may be used in a database query to access the patient treatment plan.

In a Position Detection Step 430, the position of a treatment volume within the patient is detected relative to a part of an Automated Patient Transporter 115, such as Transporter Position Sensor 225. This detection is accomplished using a two dimensional x-ray imager, a three dimensional x-ray imager, an ultrasonic imager, markers on or within a patient, markings on Patient Support 215, and or the like. The detected position is optionally stored in Position Storage 330.

In an optional Treatment Area Identification Step 440, one of Treatment Areas 105 is selected for treating the patient. This selection may be based on availability of the treatment area, a particular Particle Beam Source 150, a particle beam position or orientation within a transport area (e.g., horizontally or vertically oriented), and/or the like. Treatment Area Identification Step 440 is optional in embodiments including only one Treatment Area 105.

In an optional Schedule Step 450, the treatment of the patient is scheduled using Scheduling Logic 360. The schedule may include a time of day for preparation and treatment, as well as characteristics of the treatment such as dosage, particle energy, particle beam nozzle, patient position, Patient Support 215, Automated Patient Transporter 115, Transport Path 120, order of treatment for different patients, and/or the like. Schedule Step 450 is optionally performed in combination with Treatment Area Identification Step 440.

In an optional Programming Step 460, one of Automated Patient Transporters 115 is programmed to move the patient to the Treatment Area 105 identified in Treatment Area Identification Step 440. This programming may include communication of data and or commands to Drive/Logic 230. Alternatively, Switches 130, guide signals, or one of the other mechanisms described herein for directing one of Automated Patient Transporters 115 along a particular Transport Path 120 may be configured in Programming Step 450.

In a Transport Step 470, the patient is transported from Preparation Area 110 along one of Transport Paths 120 to one of Treatment Areas 105, using Automated Patient Transporter 115. Automated Patient Transporter 115 is typically automated in that it travels along a predetermined member of Transport Paths 120 without requiring real-time human intervention. Position Detection Step 430 is optionally performed and/or repeated following and/or as part of Transport Step 470.

In a Position Step 480, the treatment volume of the patient is positioned within one of Treatment Areas 105 relative to a therapeutic radiation beam. This positioning is typically performed using Automated Patient Transporter 115 and without removing the patient from Automated Patient Transporter 115. For example, in various embodiments, the positioning of the patient relative to the therapeutic radiation beam is accomplished using Driver/Logic 230 and/or Wheels 235.

In some embodiments, Patient Support 215 is configured to move relative to Transport Section 210 in order to position the patient. This relative movement may be accomplished such that the position of the treatment volume relative to Transporter Position Sensor 225 remains known. For example, if Patient Support 215 is raised 5 millimeters relative to Transport Section 210, a new position of the treatment volume relative to Transporter Position Sensor 225 can be calculated using this 5 millimeter displacement. Typically, the relative movement of Patient Support 215 and Transport Section 210 is accomplished under the control of Driver/Logic 230 and/or by a mechanical system, e.g., adjustable embodiments of Braces 220, included in Automated Patient Transporters 115. This mechanical system may include hydraulics, levers, motors, drive systems, encoders, and/or the like. Further details of how Patient Support 215 may be moved relative to Transport Section 210 are discussed in U.S. patent application Ser. No. 11/415,974.

In a Treatment Step 490, Particle Beam Generator 140, or some other radiation source, is used to generate a therapeutic radiation beam that is directed along one of Beam Paths 145 to the patient. This radiation beam may include high energy particles, x-rays, or any other therapeutic radiation. Following Treatment Step 490, Automated Patient Transporter 115 is optionally configured to return the patient to Preparation Area 110 along one of Transport Paths 120, where the patient may be removed from Patient Support 215.

Several embodiments are specifically illustrated and/or described herein. However, it will be appreciated that modifications and variations are covered by the above teachings and within the scope of the appended claims without departing from the spirit and intended scope thereof. For example, while particle beams and x-ray beams are presented herein as examples, other types of therapeutic and imaging systems may be alternatively or additionally be included in various embodiments.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

What is claimed is:

1. A treatment system comprising:
a particle beam source configured to generate a therapeutic beam of particles;
a particle beam nozzle to direct the therapeutic beam of particles in a first treatment area; and
an automated patient transport configured to transport a patient on a patient support from a preparation area to the first treatment area and to position a treatment volume within the patient relative to the therapeutic beam of particles, and configured to support the patient in receiving the therapeutic beam of particles, the automated patient transport including a position sensor providing signals for determining positions of the sensor and configured for use in determining the relative positions of the treatment volume and the therapeutic beam of particles,
wherein the preparation area is protected from radiation generated within the first treatment area by one or more barriers including shielding, and the patient support is integrally connected to the patient transport and inseparable from the patient transport in transporting the patient, positioning a treatment volume within the patient, and supporting the patient in receiving the therapeutic beam of particles.

2. The treatment system of claim 1 further comprising a control system configured to direct the patient transport to move.

3. The treatment system of claim 2 wherein the control system is configured to direct the patient transport to move based on at least signals received from the position sensor in the patient transport.

4. The treatment system of claim 1, wherein the position sensor is configured to position the treatment volume relative to the therapeutic beam of particles to within +/−2.0 millimeters.

5. The treatment system of claim 1, wherein the first treatment area is one of a plurality of treatment areas and the patient transport is configured to transport the patient to any one of the plurality of treatment areas responsive to a control system.

6. The treatment system of claim 1, wherein the first treatment area is one of a plurality of treatment areas and the patient transport is configured to transport the patient to any one of the plurality of treatment areas responsive to a treatment plan.

7. The treatment system of claim 1, wherein the automated patient transport is further configured to alternatively position the treatment volume relative to a plurality of therapeutic beams of particles within the first treatment area.

8. The treatment system of claim 1, wherein the automated patient transport is further configured to transport the patient from the first treatment area back to the preparation area.

9. A method comprising:
generating position information by detecting a position of a treatment volume of a patient relative to a position sensor of an automated patient transporter including a patient support supporting the patient;
transporting the patient from a preparation area to a treatment area using the automated patient transporter, the preparation area being protected from radiation generated at the treatment area by one or more barriers including shielding;

determining a position of the automated patient transporter within the treatment area using the position sensor;

positioning the treatment volume relative to a treatment beam disposed within the treatment area, using the automated patient transporter, a position of the treatment volume relative to the treatment beam being determined using the position information; and delivering a therapeutic beam to the treatment volume in the patent, the patient being supported by the automated patient transporter during the delivery of the therapeutic beam, wherein the patient support is integrally connected to the patient transporter and inseparable from the patient transporter in transporting the patient, positioning a treatment volume within the patient, and supporting the patient in delivering the therapeutic beam.

10. The method of claim 9, wherein the automated patient transport is configured to alternatively receive members of a plurality of patient supports including a patient support configured to support the patient in a sitting position and a patient support configured to support the patient in a supine position.

11. The method of claim 10, further including selecting the treatment area from among a plurality of alternative treatment areas.

12. The method of claim 10, further including programming the automated patient transporter to transport the patient to the treatment area.

13. The method of claim 10, further including programming a transport path for use by the automated patient transporter to guide the patient transporter to the treatment area.

14. The method of claim 9, further including identifying the patient.

15. The method of claim 14, further including using an identity of the patient to access a treatment plan.

16. The method of claim 14, wherein the treatment plan includes characteristics of the treatment volume.

17. The method of claim 14, further including using the treatment plan to control the treatment beam.

18. The method of claim 14, further including using the treatment plan to select the treatment area from a plurality of alternative treatment areas.

19. The method of claim 9 wherein the automated patient transporter transporting the patient is directed by a control system.

20. The method of claim 19 wherein the control system directs the patient transporter based on at least signals received from the position sensor in the patient transport.

21. The method of claim 9, wherein the automated patient transport is configured for transporting the patient in alternatively a supine or sitting position.

22. A treatment system comprising:
a radiation source configured to generate a therapeutic beam of radiation;
a treatment head to direct the therapeutic beam of radiation in a first treatment area; and
an automated patient transport configured to transport a patient on a patient support from a preparation area to the first treatment area and to position a treatment volume within the patient relative to the therapeutic beam of radiation, and configured to support the patient in receiving the therapeutic beam of radiation, the automated patient transport including a position sensor providing signals for determining positions of the sensor and configured for use in determining the relative positions of the treatment volume and the therapeutic beam of radiation,
wherein the preparation area is protected from radiation generated within the first treatment area by one or more barriers including shielding, and the patient support is integrally connected to the patient transport and inseparable from the patient transport in transporting the patient, positioning a treatment volume within the patient, and supporting the patient in receiving the therapeutic beam of radiation.

23. The treatment system of claim 22 further comprising a control system configured to direct the patient transport to move.

24. The treatment system of claim 23 wherein the control system is configured to direct the patient transport to move based on at least signals received from the position sensor in the patient transport.

25. The treatment system of claim 22, wherein the position sensor is configured to position the treatment volume relative to the therapeutic beam of radiation to within +/−2.0 millimeters.

26. The treatment system of claim 22, wherein the first treatment area is one of a plurality of treatment areas and the patient transport is configured to transport the patient to any one of the plurality of treatment areas responsive to a control system.

27. The treatment system of claim 22, wherein the first treatment area is one of a plurality of treatment areas and the patient transport is configured to transport the patient to any one of the plurality of treatment areas responsive to a treatment plan.

28. The treatment system of claim 22, wherein the automated patient transport is further configured to alternatively position the treatment volume relative to a plurality of therapeutic beams of radiation within the first treatment area.

29. The treatment system of claim 22, wherein the automated patient transport is further configured to transport the patient from the first treatment area back to the preparation area.

* * * * *